United States Patent [19]

McKay et al.

[11] Patent Number: 4,601,208
[45] Date of Patent: Jul. 22, 1986

[54] OPTICAL FIBER PROOF TESTING EQUIPMENT

[75] Inventors: Glen McKay; Henry F. Smith; Ronald W. Price, all of Saskatoon; Firoz A. Keshavjee, Nepean, all of Canada

[73] Assignee: Northern Telecom Limited, Montreal, Canada

[21] Appl. No.: 700,436

[22] Filed: Feb. 11, 1985

[30] Foreign Application Priority Data

May 18, 1984 [CA] Canada .................................. 454762

[51] Int. Cl.$^4$ ............................................. G01N 3/08
[52] U.S. Cl. ................................................. 73/829
[58] Field of Search .................. 73/829, 828, 830, 831

[56] References Cited

U.S. PATENT DOCUMENTS 1,776,514  9/1930  Laetsch et al. ........................ 73/829
4,148,218  4/1979  Knowles et al. ...................... 73/829

FOREIGN PATENT DOCUMENTS 725731  3/1955  United Kingdom .................. 73/829

Primary Examiner—Anthony V. Ciarlante
Attorney, Agent, or Firm—Stuart L. Wilkinson

[57] ABSTRACT

Optical fiber proof testing equipment has a rotary drive and two pulleys directly coupled to the drive. A fiber is taken from fiber drawing equipment around part of the circumference of the first pulley, along a guide track and around part of the circumference of the second pulley. Respective continuous belts apply a resilient bias to clamp the fiber to the pulleys, the resilient bias being adjustable. The second pulley is marginally greater in diameter than the first pulley so as to establish a predetermined tensile stress in fiber moving between the two pulleys. The test equipment is used after fiber has been drawn in a drawing tower and then coated and before the fiber is stored on reels. The tensile force on the fiber can be changed by changing the diameter of the first or second pulleys. In addition some incremental change in the tensile force can be obtained by adjusting the resilient bias provided by the continuous belt.

9 Claims, 3 Drawing Figures

OPTICAL FIBER PROOF TESTING EQUIPMENT

This invention relates to a fiber proof testing equipment and particularly to such equipment adjusted for in-line use in a fiber manufacturing plant.

In the manufacture of optical waveguides for use in optical communication systems conventionally a large diameter glass preform is made with the desired composition and the cylindrical preform is then heated to softening and fiber of the order of 125 microns in diameter is drawn from one end of the cylindrical preform. The fiber is taken to a fiber winding station where it is wound onto reels. At a stage intermediate the pulling of fiber and its storage the fiber is coated with a protective layer of a plastic such as silicone or acrylate and is coated with a powder so that the fiber can move easily relative to supporting parts of an optical cable when the fiber is made up into cable.

In order to assess whether the fiber is suitable for cabling, tests must be performed on it. One of the primary tests is to ensure that the fiber can stand up to tensile stresses which can occur while the fiber is being cabled or when the cable is being installed. A convenient way of testing all fiber made during a production run is simply to draw fiber from the fiber pulling and coating stations using drawing equipment which automatically introduces a predetermined tensile force in the fiber as the fiber passes through the drawing equipment. If the fiber is weak, it breaks.

Conventionally known equipments for in-line drawing and testing of optical fiber are of the type described in U.S. Pat. No. 4,148,218. This patent shows a first tractor assembly driven by a variable speed drive motor with the belt extending to a constant torque device, the output of which drives a second tractor assembly. The constant torque device includes a clutch and a drive including a shaft connected to a belt wheel of the second tractor assembly. The unloaded speed of this drive is faster than the rotational speed of the first tractor assembly. However when the second tractor assembly pulls the fiber, its speed is reduced by causing the constant torque device to overload and the clutch to slip. In order for the tension to stay uniform the performance of the constant torque device should not vary. However with wear, it is inevitable that the particular torque at which the clutch starts to slip will change and then either the fiber will not be tested at the right tensile stress level or the equipment must be periodically adjusted to restore the torque level.

According to the present invention there is provided an optical fiber proof testing equipment comprising a drive means, first and second pulleys directly coupled to the drive means, first resilient means for bearing down on a fiber located between the first resilient means and the pulley over part of the circumference of the first pulley to fix the fiber against that circumferential part of the first pulley, second resilient means for bearing down on a fiber located between the second resilient means and the second pulley over part of the circumference of the second pulley to fix the fiber against that circumferential part of the second pulley, guide means for guiding the fiber from the first pulley part to the second pulley part, the second pulley being larger in diameter than the first pulley.

Preferably the pulleys are fixed at the same vertical height with axes thereof parallel to one another. Each resilient means is preferably a continuous belt extending around three pulleys, a part of the continuous belt extending between two of the pulleys bearing against said circumferential part of the respective pulley. The position of the third pulley within the continuous belt can be moved towards or away from the length of belt in order to change the tension within the belt and so alter the pressure exerted by the length of the belt on the fiber extending around the pulley surface.

The guide means can be a grooved body. The grooved body can include a drop piece moveable away from the fiber to enable a direct measurement of fiber tension to be made. The fiber entry and take up positions are preferably such that the fiber extends around a quarter of the circumference of each pulley.

Preferably drive to the main pulleys is by means of a toothed band which engages a toothed drive gear.

The surface of the primary first and second pulleys can be anodized aluminum but may be coated for example with polyurethane of shore hardness of the order of 90 durometers.

An embodiment of the invention will now be described by way of example with reference to the accompanying drawings in which:-

Figure 2:
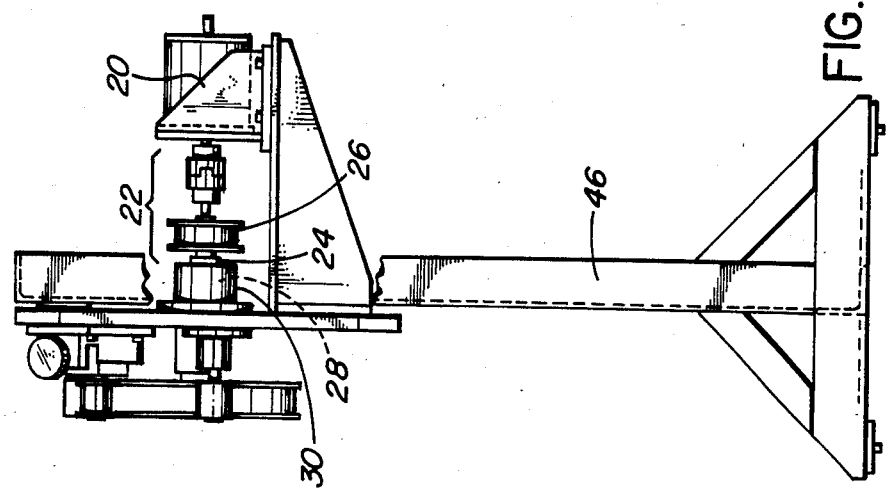
FIG. 2 is a side view of the equipment of FIG. 1.
Figure 1:
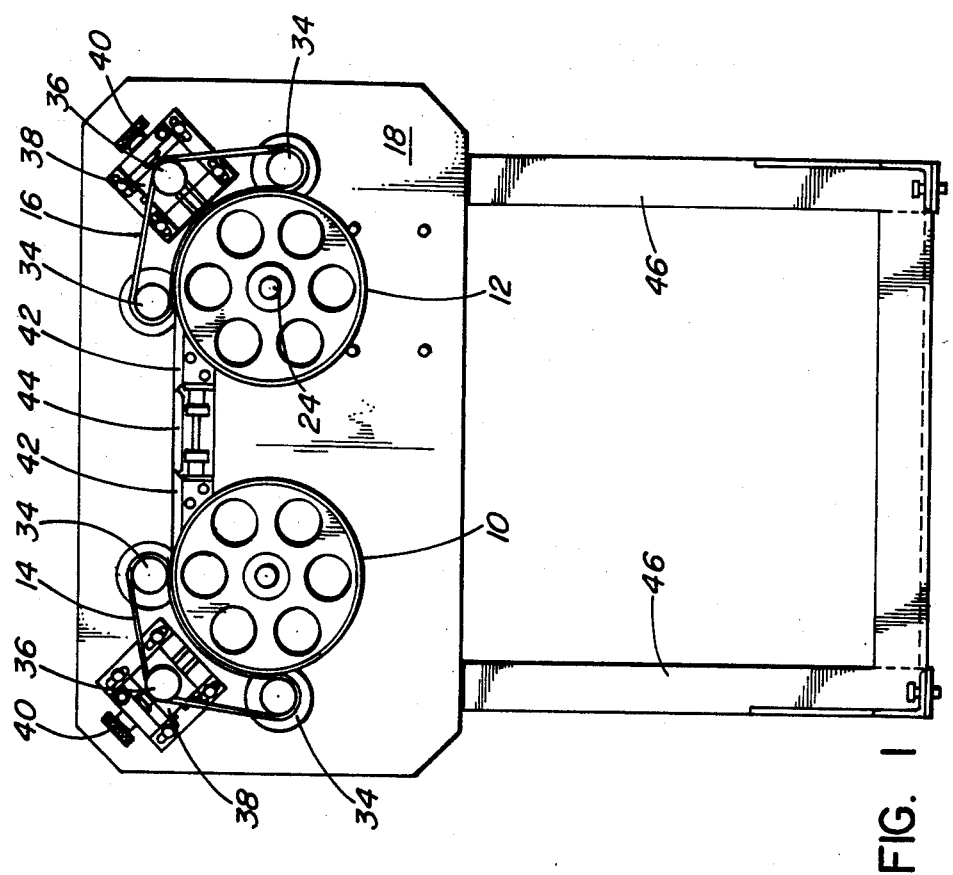
FIG. 1 is a front view of a fiber tensile test equipment according to the invention.

Referring in detail to the Figures, there is shown a pair of pulleys 10, 12. Optical fiber from a drawing and coating tower 13 is fed between the pulley 10 and a continuous flexible band 14 which presses the fiber against the pulley 10. The fiber passes along a horizontal track to the take up pulley 12 against which the fiber is pressed by a resilient band 16. The fiber extending between the two pulleys 10 and 12 is subjected to a tensile force which depends on the difference between diameters of the two pulleys and to some extent on the clamping force between the respective pulleys 10, 12 and the bands 14, 16 which bear against them.

The tensile test equipment is mounted on a panel 18. To the rear of the panel and mounted on a platform is a motor DC 20 which acts through a coupling 22 to a shasft 24 on which is mounted a toothed gear wheel 26 and elements 40 cooperate to permit adjustment of the shaft being mounted in a bearing housing 28. The toothed gear wheel 26 is secured to the shaft 24 on which is mounted the take up pulley 12. A toothed transmission band 30 extends around the toothed gear and around an identical toothed gear (not shown) which is secured to a shaft 32 on which is mounted the pulley 10. The toothed interengagement between the band 30 and the two gear wheels ensures that regardless of change in motor speed, the two pulleys 10 and 12 rotate at identical rotational velocities. The pulleys 10, 12 can be made of an apertured lightweight aluminum alloy to minimize their moments of inertia.

In use, fiber extends around part of the circumference of both pulleys and occassionally in use the fiber will slip relative to the pulley surfaces. To prevent any wear to the pulley surfaces especially if relatively hard fiber coating such as acrylate are used, the surface of the pulleys is coated with 90 durometer polyurethane. The fibers are pressed against the surface of the pulleys by the continuous bands 14 and 16 which are made of layered synthetic rubber material which is reinforced with nylon. Suitable material is available under the trade mark Habasit. The bands 14 and 16 each extend around a pair of fixed rollers 34 and a third roller 36 which is mounted on a carriage 38. The positions of carriages 38 can be adjusted in a direction radial to the associated pulleys 10, 12 by turning an adjusting screw 40. Between the two pulleys 10, 12 the fiber extends along a grooved guide having two fixed sections 42 and a central section 44 which can be detached and dropped out of the line of the guide way to allow the actual tensile force within the fiber to be routinely measured using a tensiometer (not shown).

Figure 3:
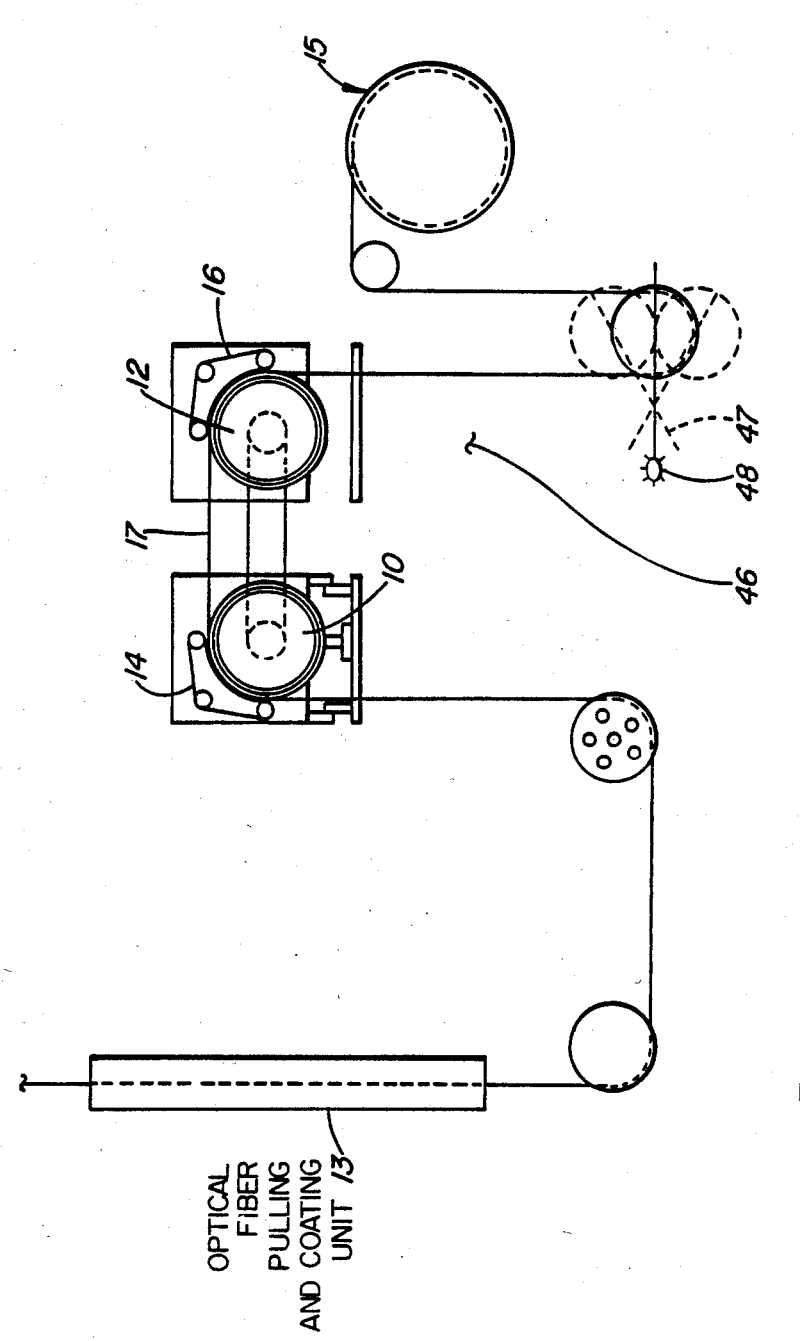
FIG. 3 is a schematic front view showing the locating of a proof tester according to the invention within a fiber manufacturing plant.

The panel 18 is bolted to a framework 46 to maintain the pulleys 10, 12 at the desired height relative to a drawing tower 13 and a fiber winding unit including reel 15 as shown in FIG. 3. The diameter of the right hand or take up pulley is made 1.19 mm greater than the diameter of the left hand pulley for a fiber stress level of 50 Kpsi. This diameter difference can be changed to vary the fiber stress level if greater or lesser stresses are anticipated during installation or cabling. The fiber is firmly held against the pulley 10 by the band 14 and since the two pulleys 10, 12 are turned at exactly the same rotational velocity then there must be some slippage of fiber on the take up pulley 12. Depending on the extent to which the fiber is biassed against a circumferential arc of pulley 12 by the band 16, this slippage is translated into a tensile force within a part 17 of the fiber stretching between the two pulleys 10, 12. To increase the tension in the fiber, the roller 36 associated with take up pulley 12 can be moved radially outward to increase the bias of band 16 against the take up roller. Adjustment screw 40 can be turned in the opposite direction to reduce tension. Alternatively, slippage promoting tension within the fiber can take place at the input pulley 10. Again by moving the reciprocal roller 36 to change the bias of the band 14 against the pulley surface lesser or greater tension within fiber part 17 can be achieved.

FIG. 3 shows the fiber being collected by the input pulley 10 from a fiber drawing and coating tower 13 and shows also the fiber leaving the output pulley 12 and being taken to the fiber take-up reel 15.

The equipment therefore not only applies a tensile stress to a fiber but is also the mechanism by means of which fiber is pulled from a preform within the pulling tower 13 down through a fiber coating unit. The equipment is normally used in conjunction with monitoring equipment located upstream of the tensile testing unit, the monitoring equipment functioning to continuously monitor the diameter of fiber and the concentricity both of the fiber core within the fiber cladding material and of the fiber itself within an applied plastic jacketing material. If there is any variation in diameter of the fiber, then the tensile testing unit can be adjusted to retard or advance the speed of drawing fiber from the preform.

As shown in FIG. 3, in the event that there is a weakness in the fiber which causes it to fracture under the applied tension, then by the fall of a dancer 47 a photodetector 48 mounted on frame 46 monitors the existence of a break and triggers an alarm. However the fiber drawing equipment continues to function. Thus the trailing section of fiber is retained by gravity within the guide groove 42 and when it reaches and is taken up by the take up pulley 12, the test tension is again applied to the remaining fiber. The alarm triggers personnel or automatic winding equipment to initiate a fiber reel transfer and reduce the pulling speed. Known tensile testing equipment of the two-pulley type have used tractor assemblies mounted one above the other so that when the fiber breaks a dangling end portion of the remaining fiber is fed from a top tractor assembly down into a bottom tractor assembly. This is inferior for three reasons. Firstly, static electricity tends to cause the fiber to wrap around the bottom pulley. Secondly, it is more difficult for the operator to rethread the fiber. Lastly, the fiber path has more bends.

What is claimed is:

1. An optical fiber proof testing equipment comprising a drive means, first and second pulleys directly coupled to the drive means, first resilient means for bearing down on a fiber located between the first resilient means and the pulley over part of the circumference of the first pulley to fix the fiber against that circumferential part of the first pulley, second resilient means for bearing down on a fiber located between the second resilient means and the second pulley over part of the circumference of the second pulley to fix the fiber against that circumferential part of the second pulley, guide means for guiding the fiber from the first pulley part to the second pulley part, the second pulley being larger in diameter than the first pulley.

2. Equipment as claimed in claim 1 in which the first and second pulleys are fixed at the same height and have axes parallel to one another.

3. Equipment as claimed in claim 1 in which each resilient means is a continuous belt extending around three idler pulleys, the idler pulleys arranged with axes parallel with one another.

4. Equipment as claimed in claim 3 in which a part of the continuous belt extending between two of the idler pulleys bears against the circumferential part of the associated first or second pulley.

5. Equipment as claimed in claim 4 in which the third idler pulley is mounted on a carriage moveable towards or away from the associated first or second pulley whereby to change tension within the continuous belt and so alter pressure exerted by the belt on fiber extending around the pulley surface.

6. Equipment as claimed in claim 1 in which the guide means is a grooved body.

7. Equipment as claimed in claim 6 in which the grooved body includes a drop piece moveable away from a fiber track to enable direct measurement of fiber tension.

8. Equipment as claimed in claim 1 in which drive to the first and second pulleys is by means of a toothed belt engaging a toothed drive gear.

9. Equipment as claimed in claim 1 in which the first and second pulleys have a surface layer adapted to combat wear from fibers sliding thereover.

* * * * *